(12) United States Patent
Zofchak et al.

(10) Patent No.: US 7,135,165 B2
(45) Date of Patent: Nov. 14, 2006

(54) MULTIPHASE SUNSCREEN COMPOSITIONS

(75) Inventors: Albert Zofchak, Holmdel, NJ (US); John C. Carson, Union City, NJ (US)

(73) Assignee: ALZO International, Inc., Sayreville, NJ (US)

( * ) Notice: Subject to any disclaimer, the term of this patent is extended or adjusted under 35 U.S.C. 154(b) by 187 days.

(21) Appl. No.: 10/300,351

(22) Filed: Nov. 20, 2002

(65) Prior Publication Data

US 2004/0096404 A1    May 20, 2004

(51) Int. Cl.
*A61K 8/00* (2006.01)
*A61K 8/18* (2006.01)
*A61K 9/00* (2006.01)
*A61K 8/02* (2006.01)
A61K 8/36 (2006.01)
A61K 8/37 (2006.01)
A61K 8/49 (2006.01)

(52) U.S. Cl. .................. 424/59; 424/60; 424/70.9; 424/400; 424/401

(58) Field of Classification Search ........... 424/400, 424/401, 59, 60, 70.9
See application file for complete search history.

(56) References Cited

U.S. PATENT DOCUMENTS

| | | | |
|---|---|---|---|
| 3,920,883 A * | 11/1975 | Yamada et al. | 514/762 |
| 4,293,305 A | 10/1981 | Wilson | |
| 4,767,741 A * | 8/1988 | Komor et al. | 512/3 |
| 5,455,035 A * | 10/1995 | Guerrero et al. | 424/401 |
| 5,468,496 A * | 11/1995 | Touzan et al. | 424/401 |
| 5,585,090 A * | 12/1996 | Yoshioka et al. | 424/59 |
| 5,635,469 A | 6/1997 | Fowler et al. | |
| 5,951,967 A * | 9/1999 | Golz et al. | 424/59 |
| 5,959,130 A | 9/1999 | Walele et al. | |
| 6,019,991 A * | 2/2000 | Tanaka et al. | 424/401 |
| 6,043,204 A | 3/2000 | Kaufman et al. | |
| 6,245,344 B1 * | 6/2001 | Thibiant et al. | 424/401 |
| 6,294,509 B1 | 9/2001 | Meiwa et al. | |
| 6,635,775 B1 * | 10/2003 | Walele et al. | 554/175 |
| 6,649,174 B1 * | 11/2003 | Najdek et al. | 424/401 |
| 6,838,077 B1 * | 1/2005 | Muller | 424/59 |
| 2002/0160023 A1 | 10/2002 | Bagdi et al. | |

FOREIGN PATENT DOCUMENTS

EP    1064926 A1 *    1/2001

OTHER PUBLICATIONS

U.S. Appl. No. 09/826,482, filed Apr. 2001, Carson et al.

* cited by examiner

*Primary Examiner*—Sreeni Padmanabhan
*Assistant Examiner*—Marina Lamm
(74) *Attorney, Agent, or Firm*—Henry D. Coleman; R. Neil Sudol; William J. Sapone

(57) ABSTRACT

The instant invention relates to novel surfactant-free, multiphase sunscreen compositions that provide protection from the sun, have a unique visual appeal, and provide skin conditioning and moisturization. In a two-phase embodiment of the instant invention, the compositions are comprised of (1) a first layer comprising a high-density ester and sunscreen, and (2) a second aqueous layer, which is usually the top layer. In a three-phase embodiment of the instant invention, the compositions are comprised of (1) a first layer comprising a high-density ester and and sunscreen, (2) a second aqueous layer, and (3) a third oily layer. The high-density ester layer usually has a specific gravity that is greater than that of the aqueous layer and the aqueous layer usually has a specific gravity that is greater than the oily layer. In preferred embodiments, each phase is substantially clear and has a volume approximately equal to that of the other phase(s). The phases disperse upon mixing and separate over time after mixing. The phases may be colored differently to enhance visual appeal. In some embodiments, emulsified boundary layer(s) form between the phases and constitute third or fourth phases.

19 Claims, No Drawings

MULTIPHASE SUNSCREEN COMPOSITIONS

FIELD OF THE INVENTION

The instant invention relates to novel surfactant-free, multiphase sunscreen compositions that provide protection from the sun, have a unique visual appeal, and provide skin conditioning and moisturization. In a two-phase embodiment of the instant invention, the compositions are comprised of (1) a first layer comprising a high-density ester and sunscreen, and (2) a second oily layer, which is usually the top layer. In a three-phase embodiment of the instant invention, the compositions are comprised of (1) a first layer comprising a high-density ester and and sunscreen, (2) a second aqueous layer, and (3) a third oily layer. The high-density ester layer usually has a specific gravity that is greater than that of the aqueous layer and the aqueous layer usually has a specific gravity that is greater than the oily layer. In preferred embodiments, each phase is substantially clear and has a volume approximately equal to that of the other phase(s). The phases disperse upon mixing and separate over time after mixing. The phases may be colored differently to enhance visual appeal. In some embodiments, emulsified boundary layer(s) form between the phases and constitute third or fourth phases.

BACKGROUND OF THE INVENTION

One portion of the solar spectrum comprises wavelengths of electromagnetic energy which range between about 290 and 3,000 nanometers (nm). This range may be divided into different regions, namely: (1) the ultraviolet region (290–400 nm), (2) the visible region (400–760 nm) and (3) the near-infrared region (>760 nm). The ultraviolet region has, moreover, been arbitrarily divided into three bands, referred to as the UVA, UVB and UVC bands.

The UVB band extends from 290 to 320 nm. It is the principal cause of the sunburn reaction and it is also the most effective in stimulating the tanning reaction in the skin. UVC radiation (200–290 nm) from the sun does not reach the surface of the earth, although one can encounter radiation in this range from artificial sources such as germicidal lamps and high and low pressure mercury arc lamps. For purposes of the present invention, however, protection against UVC radiation is generally not a major concern, i.e., in contrast to the dangers posed by UVA and UVB radiation. The UVA band, which extends from 320–400 nm, can also cause the tanning reaction. UVA radiation can also cause sunburns, but its capacity to do so is less than that of UVB radiation.

The amount of UVA radiation exposure, however, is increasing. This is due to the fact that most sunscreens effectively block only UVB radiation. As stated above, UVB radiation is more capable than UVA radiation of causing the tanning and burning reactions. Therefore, if one is using a sunscreen that blocks UVB radiation he/she will tend to stay in the sun for an extended period of time because the immediate effects of the sun tan/burn are not evident. The problem is that UVA is still penetrating the skin and although it is not causing any immediately obvious effects, it is causing long-term damage. Long-term hazards of ultraviolet radiation include premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging).

In recent years, it has been well documented that UVA radiation, like UVB radiation, is harmful to the skin. In fact, current data reveal that solar radiation containing these wavelengths (A and B) is a contributing cause of skin cancer, which presently accounts for 30–40% of all new cancers each year. In the United States alone, 500,000 new cases of skin cancer will be reported this year and the number is expected to keep rising in the future. UVA radiation has been shown to promote skin cancer by inhibiting enzymes that repair cells damaged by UVB radiation. UVA radiation also penetrates more deeply into the skin than UVB radiation and causes changes in blood vessels and premature aging of the skin, thus adding to the damage produced by UVB rays. The goal of any sunscreen should thus be to protect the user from both UVA and UVB radiation with a minimum of side effects.

The "SPF" (Sun Protection Factor) is recognized as the ratio of the irradiation time required to elicit a minimum erythemal reaction (sunburn) on sunscreen protected skin using a solar simulator, to the irradiation time required to elicit the same minimum erythemal reaction (sunburn) on unprotected skin. This test is conducted under clinical conditions according to the procedure described in the Proposed Monograph for Sunscreen Containing Drug Products (hereafter referred to as the Proposed Monograph) published by the U.S. Food and Drug Administration (FDA) in the U.S. Federal Register, Vol. 43, Aug. 25, 1978, Part 2, pages 38206–38269, which is incorporated herein by reference. As used herein, the term "SPF" or Sun Protection Factor is defined in accordance with the definitions in the Proposed Monograph. This same publication also describes the clinical testing procedure mandated for determining whether sunscreen products are waterproof, water resistant and sweatproof. The labeled SPF values are generally recognized as being between 2 and 50. This is not meant to imply that SPF values greater than 50 are unachievable given the previous formulation technology. However, the amounts of sunscreen agents needed to achieve such high SPF values are usually cost prohibitive given current formulation technologies. The concentration of sunscreen agents needed to satisfy a waterproof designation are particularly high, because some of the agents are washed away in the test that measures SPF for a waterproof composition.

In general, the SPF number approximately corresponds to the multiple of time during which the properly applied sunscreen will prevent obvious reddening of the skin, over the exposure time that causes unprotected skin to exhibit reddening. Thus, a person should be able to remain in the sun without visible effects for eight times the usual unprotected duration, if an SPF 8 sunscreen formulation has been properly applied. Of course, the duration of unprotected exposure, which produces a visible effect on the skin, varies from one individual to another, due to differences in their skin cells. Currently popular are high-SPF "sunblocker" products, having SPF values of at least 30.

A sunscreen works on the surface of the skin to absorb UV radiation so that the harmful rays never enter the skin. Commercially available sunscreen products contain from about 3 to about 26% of one or more UV absorbing chemicals. When applied to the surface of the skin as a thin film, these chemicals act as a filter to diminish the penetration of UV radiation to the cells of the epidermis. These sunscreens are typically applied in a cream, oil, lotion, alcohol or gel vehicle and they are usually colorless because they do not contain any visible light-absorbing chemicals. The most widely used organic-based sunscreens contain, for example, paraminobenzoic acid (PABA), PABA esters (glyceryl PABA), amyldimethyl PABA and octyldimethyl PABA), benzophenones (oxybenzone and sulisobenzone), cinnamates (octylmethoxy cinnamate and cinoxate), salicylates (homomethyl salicylate), anthranilates such as menthyl anthranilate, 2-ethylhexyl-2-cyano-3,3-diphenyl acrylate, 2-phenyl benzimidazole-5-sulfonic acid, digalloyl trioleate, 3-(4-methyl benzylidene) camphor, 4-isopropyl dibenzoyl methane, butyl methoxy dibenzoyl methane, 2-ethyl-2-cyano-3,3'-diphenyl acrylate.

Common sun care products sold in today's market include oil-in-water emulsions incorporating stearic acid neutralized with triethanolaminc. The SPF values of such emulsions range from 2 to 50, and they commonly include ethylhexyl methoxycinnamate as the sunscreen agent. As the SPF of these formulations increases, they commonly contain ethylhexyl salicylate, homosalate, octocrylene and/or oxybenzone in addition to the ethylhexyl methoxycinnamate mentioned above. Alternatively, padimate O can be used in place of the ethylhexyl methoxycinnamate or the salicylates mentioned above. Dioxybenzone, avobenzone or menthyl anthranilate can be used in place of oxybenzone. If the product does not claim to be substantive to the skin (i.e., waterproof or water resistant), trolamine salicylate or DEA methoxycinnamate can be used in place of (or in combination with) the ethylhexyl methoxycinnamate, ethylhexyl salicylate or homosalate. Additionally, sulisobenzone may be used in such non-substantive formulations in place of oxybenzone. The Proposed Monograph lists 21 active ingredients that can be used individually or in combinations to achieve the desired product SPF.

U.S. Pat. No. 4,917,882 ("'882 patent") discloses a gel-type sunscreen composition comprising about 1 and about 30 percent of sunscreen agent, between about 5 and about 25 percent polyethylene, and between about 20 and about 95 percent of a benzoate ester. The benzoate ester is important to the composition of the '882 patent because it provides a translucent, non-oily feeling, anhydrous vehicle which is well suited for carrying the sunscreen agents. In particular, the patent notes that benzoate esters do not interfere with the UV absorption of typical sunscreen agents and that compounds such as mineral oil have been found to shift the absorbance curve of agents such as Padimate O, thereby reducing their ability to absorb UV radiation in the erythemal region.

Sunscreen compositions in the form of creams and lotions are two-phase systems in which one of the phases is finely and uniformly dispersed within the other to form an emulsion. Mixing the two phases with an appropriate surfactant emulsifier, which also functions to stabilize the emulsion and initially makes the dispersion. The sun screening ingredients are usually solubilized in the oil phase, which is, most commonly, the internal or dispersed phase. However, after application and prolonged exposure of the skin to water, the surfactants actually facilitate the emulsifier removal of the product from the skin by causing the oils to re-emulsify.

Several approaches have been taken in an effort to solve this problem. One solution is to resort to water in oil emulsions. Because this type of emulsion is usually not sufficiently water soluble to dissolve or disperse in water, it therefore has little ability to re-emulsify oily material into water. Another technique used to reduce the re-emulsification of the sunscreen's internal "oily phase" is to use emulsifiers that lose their ability to emulsify once they have been applied to the skin. These are typified by the "polymeric" surfactants that rely upon a "sphere of hydration" to establish and maintain their water solubility. Once the hydration sphere is lost (due to drying when the product is applied to the skin), the polymeric surfactant loses its ability to emulsify and the oil phase along with the dissolved sunscreens stay on the skin.

Another way to eliminate re-emulsification is to simply not include any surfactants in the formulation. Sunscreen oils take this approach and do not show significant reductions in sun protection factors following bathing. However, sunscreen or sun tanning oils are considered to have an unpleasant, "greasy" feel and they can have an unfavorably high cost of goods as they are made entirely of oils. Creams and lotions, on the other hand, can contain 70% to 80% water and therefore have a concomitantly lower production cost, but they suffer from the re-emulsification problem described above.

The need exists, therefore, for multiphase, high SPF sunscreen compositions that provide adequate and prolonged protection against both UVB and UVA radiation even upon extended exposure to water. Ideally, such compositions would have a low production cost and would not evoke any unpleasant sensation upon application to the skin. Further, the need exists for multiphase sunscreen products in which the various phases are visibly distinct prior to application, thereby enhancing the cosmetic appeal of the products.

OBJECTS OF THE INVENTION

It is an object of the present invention to provide multiphase sunscreen compositions with a high SPF value that ensure adequate and prolonged protection against both UVA and UVB radiation, even upon extended exposure to water.

It is a further object of the present invention to provide multiphase sunscreen compositions that have a high SPF and that (i) ensure adequate and prolonged protection against both UVA and UVB radiation even upon extended exposure to water, (ii) have a low production cost, and (iii) do not evoke any unpleasant sensation upon application to the skin.

It is a further object of the present invention to provide novel multiphase sunscreen compositions in which (i) all phases are liquid, (ii) all phases are separated according to differences in specific gravity, and (iii) in which the different phases and may optionally be colored differently for cosmetic purposes.

It is another object of the instant invention to provide a multiphase sunscreen system in which the various phases disperse uppn mixing and separate over time after mixing.

It is a still further object of the present invention to provide a novel multiphase sunscreen system in which phase separation is maintained during packaging.

SUMMARY OF THE INVENTION

In accordance with the above-stated objects, the instant invention provides two and three phase sunscreen systems comprising high-density esters, sunscreens, water, and emollients. Sunscreen compositions of the instant invention have been found to possess remarkable substantivity, even when immersed in water for prolonged periods. Accordingly, the preferred compositions of the present invention can be designated as "waterproof" or "water resistant" under the guidelines published in the Proposed Monograph.

The instant invention also provides the advantage that, unlike most anhydrous gel-type compositions, the composition has a generally non-greasy feel to it. Further, compositions of the instant invention can be made with an aesthetically pleasing appearance and can include dyes and the like to impart desirable colors, e.g. a bronzing color, to the composition. Humectants, hydrotropes, thickeners, phase separation enhancers, solvents, and fragrances may be added as needed to the compositions.

More specifically, a two-phase sunscreen composition of the instant invention comprises a blend of:
(a) about 2% by weight to 15% by weight of a high density ester;
(b) about 5% by weight to about 25% by weight of a sunscreen;
(c) about 5% by weight to 25% by weight of one or more emollients; and
(d) about 40% to 90% by weight of water.

Definitions and examples of these components are provided hereinafter. The blend comprises a first layer comprising a high-density ester and sunscreen and a oily layer comprising water and one or more emollients. The first and second layers substantially disperse upon mixing and separate over time after mixing. During storage, the first high-density ester-sunscreen layer usually separates to the bottom of a container. Cyclic polyalkylsiloxanes (preferably cyclomethicone), dispersing agents, cosmetic esters, humectants, hydrotropes, thickeners, phase separation enhancers, fragerences, and dyes may also be added to the sunscreens. The specific gravity of the first high-density ester-sunscreen layer is typically greater than that of the second (water), and each layer is usually substantially distinct from the other. However, addition of salts to the water layer can increase its specific gravity to a value greater than that of the high-density ester layer with the result that the water layer becomes the bottom layer.

A three-phase sunscreen product of the instant invention comprises three substantially distinct liquid layers. The top most layer typically comprises one or more oily emollients and cyclic polyalkylsiloxanes, and may also contain dispersing agents, cosmetic esters, humectants, hydrotropes, thickeners, phase separation enhancers, solvents, fragerences, and dyes. The middle phase is typically an aqueous (water) phase and may contain ingredients to adjust specific gravity and ionic strength. This middle layer facilitates dilution of active sunscreen ingredients and provides moisturization and humectancy for the skin. The bottom layer is typically comprised of a high-density ester and sunscreen actives.

More specifically, a three-phase sunscreen composition of the instant invention comprises a blend of:
(a) about 2% by weight to 15% by weight of a high-density ester;
(b) about 5% by weight to about 25% by weight of a sunscreen;
(c) about 5% by weight to 25% by weight of one or more emollients and cyclic polyalkylsiloxanes; and
(d) about 40% to 90% by weight of water.

The blend comprises a first or bottom layer comprising the high-density ester and sunscreen, a second aqueous layer comprised substantially of water, and a third oily layer comprising the emollient and cyclic polyalkylsiloxane. The specific gravity of the first high-density ester layer is typically greater than that of the second aqueous layer and third oily layer and the specific gravity of the second aqueous layer is typically greater than that of the third oily layer. However, addition of salts or thickeners to the aqueous layer can increase its specific gravity to a value greater than that of the high-density ester layer, with the result that the aqueous layer becomes the bottom layer. Alternatively, addition of alcohols to the aqueous layer can actually reduce its specific gravity relative to that of the oily layer with the result that the aqueous layer becomes the top layer. Preferably, each layer is substantially distinct from the other and can be colored differently to provide a visually appealing as well as functionally effective sunscreen and skin conditioning system. The first, second, and third layer substantially disperse upon mixing and separate over time after mixing.

In a novel aspect of the present invention, the high-density esters employed in the first layer cause a phase separation between the otherwise miscible sunscreen and emollient ingredients. High-density esters used in the formulations of the instant invention include esters having a specific gravity greater than about one which are formed by the reaction of aromatic alcohols or acids. Benzoic acid esters of diols, triols, and tetraols may be used as high-density esters. Benzoate esters of propylene glycol and dipropylene glycol, e.g., dibenzoate esters of dipropylene glycol, are preferred. Various materials that provide emolliency, skin protection, or enhance the moisturization of the skin can be added to the oily layer and ingredients that adjust specific gravity and ionic strength can be added to the aqueous layer.

Compositions of the instant invention are shaken prior to application to mix and temporarily disperse the phases. Phase separation is not immediate in order to allow sufficient time for product application. The separation time can be controlled by appropriate adjustment of the specific gravity differences between the phases. The smaller the differences in specific gravity between the phases, the longer the time will be to complete phase separation. The product is then dispensed and applied to the skin. When left to stand after shaking, the product will again separate into three discrete phases.

Sunscreens of the instant invention preferably create the distinct impression of having multiple phases. Therefore, it is a desirable, but not necessary, feature of the invention that all phases become clear upon separation. Also, it is a desirable, but not necessary, feature of the invention that the phase separation occurs at a moderate pace after having been mixed in order to allow for application of the sunscreen. It is also a desirable, but not necessary, feature of this invention that the individual layers be individually and uniquely colored to enhance the appearance of separation.

The viscosity of the phases may also be adjusted in order to control separation; separation times increase with increasing viscosity. Thickening the water phase through the addition of thickeners such as water-soluble polymers defined hereinafter is the most effective means of increasing viscosity, as the water phase is the continuous phase in most compositions of the instant invention. Thickeners may also be added to the emollient (oil) phase to adjust viscosity. Examples of other suitable thickeners are provided hereinafter.

General guidelines to ensure rapid component separation to form clear, liquid phases include the following.

1. Choose components that have large differences in densities. According to Stokes Law, when a sufficiently small spherical particle falls in a viscous fluid, such that the fluid may be assumed to undergo a quasistatic viscous flow (very low Reynolds number), the drag on the fluid is given by:

$$\text{drag force} = 3\pi\rho dw$$

where $\mu\rho$ is the fluid viscosity, d the particle diameter, and w the settling velocity. Therefore, the greater the density differences between phases, the faster the separation.

2. Keep all phase viscosities to a minimum Again, Stokes Law is applicable and dictates that lower viscosities facilitate rapid phase separation.

3. Add phase separation enhancers, as defined hereinafter.

The use of some or all of these methods to improve separation can result in formulations that will separate as desired.

DETAILED DESCRIPTION OF THE INVENTION

It is noted that, unless otherwise indicated, the percentages disclosed herein refer to percentages by weight of the total sunscreen composition.

As used herein, the following terms have the following meanings.

"Cosmetic esters" include $C_1$–$C_{30}$ alcohol esters of $C_1$–$C_{30}$ carboxylic acids and of $C_2$–$C_{30}$ dicarboxylic acids, including straight and branched chain materials as well as aromatic derivatives (as used herein in reference to the hydrophobic component, mono- and poly-carboxylic acids include straight chain, branched chain and aryl carboxylic acids). "Cosmetic esters" can function as "Emollients" as defined herein. Nonlimiting examples of cosmetic esters include diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenate, dioctyl maleate, dioctyl sebacate, dioctyl adipate, cetyl octanoate, and diisopropyl dilinoleate.

"Cosmetic esters" also include $C_2$–$C_{30}$ mono- and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates: behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose.

"Cyclic polyalkylsiloxanes" suitable for use in the composition include those represented by the chemical formula $[Si(R)_2—O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclic polydimethylsiloxane or cyclomethicone (according to the CTFA nomenclature Cosmetic Ingredient Dictionary, published by the Cosmetic, Toiletry and Fragrance Association, Inc., 1110 Vermont Avenue, NW, Wash. D.C. 20005, Third Edition 1982). Commercially available cyclomethicones include Dow Corning SF 344 fluid having a viscosity of 2.5 centistokes, and a boiling point of 172° C., which primarily contains the cyclomethicone tetramer (i.e. n=4), Dow Corning SF 345 fluid having a viscosity of 2.5 centistokes and a boiling point of 178° C., which primarily contains the cyclomethicone pentamer (i.e. n=5), Dow Corning SF 344 fluid having a viscosity of 4.2 centistokes and a boiling point of 205° C., which primarily contains a mixture of the cyclomethicone tetramer and pentamer (i.e. n=4 and 5), and Dow Corning SF 245 fluid having a viscosity of 4.5 centistokes and a boiling point of 217° C. which primarily contains a mixture of the cyclomethicone tetramer, pentamer, and hexamer (i.e. n=4, 5, and 6).

"Emollients" are dermatologically acceptable compositions that tend to lubricate the skin, increase the smoothness and suppleness of the skin, prevent or relieve dryness of the skin, and/or protect the skin. Emollients are typically water-immiscible, oily or waxy materials. A wide variety of suitable emollients are known and may be used herein. These include emollients may be selected from one or more of the following classes: triglyceride esters which include, but are not limited to, vegetable and animal fats and oils such as castor oil, cocoa butter, safflower oil, cottonseed oil, corn oil, olive oil, cod liver oil, almond oil, avocado oil, palm oil, sesame oil, kikui oil, and soybean oil; Acetoglyceride esters, such as acetylated monoglycerides; Ethoxylated glycerides, such as ethoxylated glyceryl monostearate; Alkyl esters of fatty acids having 10 to 20 carbon atoms which include, but are not limited to, methyl, isopropyl, butyl, hexyl, isohexyl, octyl and higher esters of fatty acids such as hexyl laurate, isohexyl laurate, isohexyl palmitate, isopropyl palmitate, methyl palmitate, decyloleate, isodecyl oleate, hexadecyl stearate decyl stearate, isopropyl isostearate, methyl isostearate, diisopropyl adipate, diisohexyl adipate, dihexyldecyl adipate, diisopropyl sebacate, lauryl lactate, myristyl lactate, and cetyl lactate; Alkenyl esters of fatty acids having 10 to 22 carbon atoms such as oleyl myristate, oleyl stearate, and oleyl oleate; Fatty acids having 10 to 22 carbon atoms such as pelargonic, lauric, myristic, palmitic, stearic, isostearic, hydroxystearic, oleic, linoleic, ricinoleic and arachidic acids; Fatty alcohols having 10 to 22 carbon atoms such as lauryl, myristyl, cetyl, hexadecyl, stearyl, isostearyl, hydroxystearyl, oleyl, ricinoleyl and 2-octyl dodecanyl alcohols; Lanolin and lanolin derivatives such as lanolin, lanolin oil, lanolin wax, lanolin alcohols, lanolin fatty acids, isopropyl lanolate, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenated lanolin, ethoxylated hydrogenated lanolin, and liquid and semisolid lanolin absorption bases; Polyhydric alcohol esters such as ethylene glycol mono and di-fatty acid esters, diethylene glycol mono-and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, sorbitan fatty acid esters, and polyoxyethylene sorbitan fatty acid esters; Wax esters such as beeswax, spermaceti, myristyl myristate, stearyl stearate, jojoba oil; Beeswax derivatives such as polyoxyethylene sorbitol beeswax which are reaction products of beeswax with ethoxylated sorbitol of varying ethylene oxide content, forming a mixture of ether esters; Vegetable waxes including, but not limited to, camauba and candelilla waxes; Phospholipids such as lecithin and derivatives; Sterols including, but not limited to, cholesterol and cholesterol fatty acid esters; and Amides such as fatty acid amides, ethoxylated fatty acid amides, and fatty acid alkanolamides.

Preferred emollients include mineral oils, aliphatic hydrocarbons, branched aliphatic hydrocarbons, squalane, squalene, cyclomethicones, dimethicones, jojoba oil and/or monoesters of fatty acids and fatty alcohols with a total of at least 36 carbons and more preferably, 40 to 44 total carbon atoms.

"Dispersing agents" used in the instant invention include but are not limited to water-insoluble alkyl esters and derivatives such as PPG2 Myristyl ether propionate, cyclomethicone, or polyhydric compounds such as glycerin.

"Fragrances" are aromatic compounds that can impart an aesthetically pleasing aroma to the sunscreen composition. Typical fragrances include aromatic materials extracted from botanical sources (i.e. rose petals, gardenia blossoms, jasmine flowers, etc.), that can be used alone or in any combination to create essential oils. Alternatively, alcoholic extracts may be prepared for compounding fragrances. One or more fragrances can optionally be included in the sunscreen composition.

"High density esters" include esters with a specific gravity greater than about one formed by the reaction of aromatic alcohols or aromatic acids. For example, high-density esters include esters formed by the reaction of benzoic acid with alcohols having from 12 to 15 carbons. One such benzoate ester is sold by FINTEX under the designation "Finsolve TN." Alternatively, benzoate esters such as "Finsolve P" and "Finsolve SB", both from FINTEX, can be used. Benzoic acid esters of diols, triols, and tetraols may be used as high-density esters. Preferred high-density esters include benzoate and, dibenzoate esters of diols including propylene glycol and dipropylene glycol, e.g., dibenzoate esters of dipropylene glycol. Octanol esters of $C_6$–$C_{18}$ fatty acids and $C_{12}$–$C_{15}$ alcohols benzoate, also referred to as $C_{12}$–$C_{15}$ alkyl benzoate, can also be used. Benzoate esters produced by the reaction of benzoic acid on the hydroxyl group of the castor-based fatty acids backbone in the form of castor oil (triglyceride), hydrogenated castor oil (castor wax), ricinoleic acid fatty alkyl ester or hydroxy stearic acid alkyl ester, such as those disclosed in U.S. Pat. No. 5,959,130 ("'130 patent"), can also be used as high density esters. The complete disclosure of the '130 patent is hereby incorporated by reference.

A 'humectant' is a moistening agent that promotes retention of water due to its hygroscopic properties. Suitable humectants include glycerin, polymeric glycols such as poyethylene glycol and polypropylene glycol, and sorbitols such as sorbitol solution. One or more humectants can optionally be included in the sunscreens of the instant invention.

"Hydrotropes" are compounds that have the ability to increase the solubility of slightly soluble organic compounds. Hydrotropes useful in the instant invention include but are not limited to ammonium, sodium and potassium xylene sulfonate salts, naphthalene sulfonate salts, sodium alkyl disulfonates, acetamido and lactamido propyltrimonium chlorides, sorbitol, glucose, sucrose, fructose, dextrose, glycerin, sorbitol ethoxylated glycerin, polyhydroxy compounds such glycols including propylene glycol, methylpropane diol, butylene glycol, hexylene glycol, ethoxy diglycol and ethoxylated glycols, alcohols including ethanol and isopropanol, glycerin, dextrose, and sorbitol.

"Solvents" used in the instant invention include ethanol, isopropanol, propanol, propyleneglycol, methyl propane diol, butylene glycols, dipropylene glycol, ethoxy diglycol and hexylene glycol.

"SPF" (Sun Protection Factor) has the meaning defined previously herein.

A "sunscreen" is an agent that, in an effective amount, reduces the amount of skin erythema resulting from exposure to ultraviolet radiation. The sunscreen agent can protect against either UVB type ultraviolet radiation or UVA type ultraviolet radiation, or both and can be an aromatic compound (such as oxybenzone and cinnamic acid derivatives) which efficiently absorb harmful ultraviolet rays. Sunscreen agents that can be used in the instant invention include but are not limited to: p-aminobenzoic acid, its salts and its derivatives (ethyl, isobutyl, glyceryl esters; p-dimethylaminobenzoic acid); anthranilates (i.e., 0-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2', 4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane.

Further examples of sunscreen agents include octyl methoxycinnamate, menthyl anthranilate, octyl salicylate, octocrylene, Padimate O (octyl p-dimethylaminobenzoate); Padimate A (amyl p-dimethylaminobenzoate); Oxybenzone (2-hydroxy-4-methoxybenzophenone); ethylhexyl p-methoxycinnamate; PABA (para-aminobenzoic acid); Cinoxate (2-ethoxyethyl p-methoxycinnamate); diethanolamine p-methoxycinnamate; digalloyl trioleate; Dioxybenzone (2,2'-dihydroxy-4-methoxybenzophenone); ethyl 4-[bis(hydroxypropyl)]-aminobenzoate; 2-ethylhexyl 2-cyano-3,3-diphenylacrylate; ethylhexyl p-methoxycinnamate; 2-ethylhexyl salicylate; glyceryl aminobenzoate; Homosalate (3,3,5-trimethylcyclohexyl salicylate); menthyl anthranilate (menthyl o-aminobenzoate); 2-phenylbenzimidazole-5-sulfonic acid); Sulisobenzone (5-benzoyl-4-hydroxy-2-methoxybenzenesulfonic acid); triethanolamine salicylate; 4-tert.butyl-4-methoxy-dibenzoylmethane; and benzalphthalide.

"Thickeners" which may be added to the water phase comprise water-soluble polymers including carboxymethylcellulose, hydroxyethylcellulose, hydroxypropylmethylcellulose, hydroxypropyl cellulose, polyoxyethylene, polyvinylalcohol, polyvinylalcohol/polyvinylacetate copolymer, polyvinylpyrrolidone, polymethacrylates and copolymers, carbomers, natural gums and modified natural gums, starches and modified starches, proteins, modified proteins and mucopolysaccharides, proteins, starches, guar gum and derivatives, acacia, agar agar, carrageenan, xanthan and their derivatives. In addition, inorganic thickening agents such as clays, silicas and silicates may be used. Thickeners which may be added to the emollient or oil phases include, for example, waxes, lipophilic polymers such as polyethylene and polypropylene, polysiloxane, silicone gum, hydrophobically treated silicas, etc. These viscosity modifications may be used individually or in combination.

"Phase separation enhancers" include sodium, ammonium, potassium, calcium and magnesium salts formed with anions such as: chloride, sulfate, nitrate, phosphate, carbonate, acetate, lactate and ethylenediaminetetraacetate, and hydrotropes such as ammonium, sodium and potassium xylene sulfonates, sodium alkyl disulfonates, solvents such as ethanol, isopropanol, ethoxy diglycol, and glycols and polyhydroxy compounds such as propylene glycol, methylpropane diol, butylene glycol, hexylene glycol, glycerin, dextrose, sorbitol, and sucrose. The ingredients used in the water phase to improve separation may or may not be exclusively soluble in the water phase. For example, ethanol has appreciable solubility in cyclomethicone and, while useful in improving phase separation and reducing specific gravity, it will also alter the phase volume ratios by partitioning into other phases in addition to the water phase. Such partitioning may also alter the solubility of specific components in that phase. For example, the solubility of a colorant in a particular phase can be increased. Added fragrances can also have similar effects upon partitioning.

A "waterproof" composition is one that exhibits its labeled SPF value after 80 minutes of exposure to water under conditions that simulate swimming for that period of time. A "water resistant" product is similarly defined, except that it must withstand 40 minutes of water exposure. Although there is a separate test for the "sweat proof" claim, the Proposed Monograph allows products that pass the waterproof or water resisitant claim to also carry the sweat proof claim.

This invention describes a unique product form for a sunscreen product that is intended for personal care use and is meant to provide protection from the harmful UV radiation emanating from the sun. As such, it must be formulated in accordance with all FDA regulations and guidelines concerning the use of UV radiation absorbers along with the mandated testing to establish a Sun Protection Factor (SPF). Thus, the nature and maximum usage levels of the sunscreening ingredients are established and must be complied with.

Preferred two phase compositions of the instant invention comprise about 5% to 25% by weight of one or more sunscreens, about 5% to 25% by weight of one or more cyclic polyalkylsiloxanes, about 2% to about 15% by weight of one or more high-density esters, about 40% to about 80% by weight water, about 5% to 15% by weight of an alcohol, and about 1% to 10% by weight of one or more of the following: glycerin, a gycol or a salt. A preferred two-phase composition comprises about 5% to 25% by weight menthyl anthranilate and octyl methoxycinnamate, about 5% to 25% by weight jojoba oil, about 2% to about 15% by weight dipropyleneglycol dibenzoate, about 50% to about 80% by weight water, about 5% to 15% by weight of an alcohol, and about 1% to 5% by weight of magnesium nitrate heptahydrate.

In addition to the foregoing ingredients and amounts, preferred three-phase compositions also contain about 5% to 25% by weight of one or more cyclic polyalkylsiloxanes. A preferred three-phase composition of the invention comprises about 5% to 25% by weight menthyl anthranilate and octyl methoxycinnamate, about 5% to 25% by weight of cyclomethicone, about 2% to about 15% by weight dipropyleneglycol dibenzoate, about 40% to about 80% by weight water, about 5% to 15% by weight of an alcohol, and about 1% to 10% by weight of one or more of the following: glycerin, a gycol, or a salt.

In formulating compositions of the instant invention, there are several general considerations that will facilitate rapid phase separation and will assist in the phases separating as clear, liquid phases. As mentioned, these include choosing components that have large differences in densities, keeping all phase viscosities to a minimum, and adding phase separation enhancers. The ingredients used in the water phase to improve separation may or may not be exclusively soluble in the water phase. The use of some or all of these methods to improve separation can result in formulations that will separate as desired.

Compositions of the instant invention are intended to be visually unique and it is an object of this invention to provide products that give the distinct impression of having multiple phases. Therefore, it is a desirable, but not necessary, feature of the invention that all phases become clear upon separation. Also, it is preferred that the phase separation occur at a moderate pace after having been mixed in order to allow for application of the sunscreen and that the individual layers be individually and uniquely colored to enhance the appearance of separation. In addition, the volume of the separated phase, or phases, must be sufficiently large so as to be readily apparent in the final package.

In any multiple phase product, there can be appreciable mutual solubility of one or several of various materials, notwithstanding efforts to minimize mutual solubility in order to achieve the separation. Further, mutual solubilities will vary with changing temperature. This variable affects the volumes of the separating phases. Therefore, it is necessary to determine empirically practical and aesthetically pleasing separated phase volumes in a multiple phase product as the formula amounts added do not necessarily reflect the phase volumes seen in the final product.

Another concern is that the solubility (or emulsifiability) of the oily phase in the aqueous phase and the solubility of the aqueous phase in the oily phase affect the clarity of the phases and the speed at which they separate. Generally, as more of the oil phase is emulsified into the water phase, the more opaque the water phase becomes. Similarly, the oil phase or phases will become more opaque as more of the aqueous phase is incorporated into them. Achieving this effect is also a matter of experimentation.

In addition to affecting the clarity of the separated phases, the partial emulsification of one phase in another phase will affect the phase volume. Thus, the amount of each phase has to be adjusted experimentally in order to establish aesthetically pleasing phase volume ratios. In preferred embodiments, the volume of the high-density ester layer comprises about 15% to 30% of the total sunscreen composition volume, the volume of the aqueous layer comprises about 30% to 70% by volume of the total sunscreen composition, and the volume of the emollient and polyalkylsiloxane layer comprises about 15% to 30% by volume of the total sunscreen composition.

An emulsified layer (or layers) may also form that can separate independently from the mutually immiscible (intentionally separating) phases. These emulsified layers usually appear at the interface between two separated layers and form an opaque "boundary layer" between two phases. While these layers are interesting and may be visually appealing, they are difficult to stabilize and maintain as a discrete entity. However, some success in creating this type of stable effect has been achieved through the use of fumed silcas, hydrophobically treated fumed silicas, finely divided (powdered) Teflon™, microfine zinc oxide (Z-Cote®) and microfine titanium dioxide (T-Cote®). In addition, the latter materials will provide sun protection as well as constituting a fourth phase.

Finally, temperature substantially affects the mutual solubilities, phase volume ratios, and clarity of the aqueous and the oil phases. Therefore, it is important to evaluate the degree and quality of phase separation at a standardized temperature, even though the products must be tested for physical and chemical stability at various temperatures.

The invention is further illustrated by the following examples, which are illustrative and in no way limiting.

EXAMPLE 1

Two-Phase Sunscreen

A two-phase sunscreen (formulation 1) was made in accordance with the instant invention using the ingredients and weight percentages listed in Table 1 below. The resultant product exhibited a two-layer separation with an oily, opaque, upper layer that represents about 40% of the total formula volume and a clear lower aqueous phase. It should be noted that magnesium nitrate is not recommended or intended for use in cosmetic products—sodium chloride is the preferred salt and should be substituted in commercial formulations made in accordance with this example.

TABLE 1

Formulation 1 (All percentages in weight percent)

| Ingredients | % |
|---|---|
| Menthyl Anthranilate | 5.0 |
| Octyl Methoxycinnamate | 7.5 |
| Jojoba Oil | 10.0 |
| Dipropyleneglycol Dibenzoate | 10.0 |
| Deionized Water | 50.0 |
| Ethanol | 14.0 |
| Magnesium Nitrate, Heptahydrate | 3.5 |
| Fragrance, Color, Preservative | QS |
| | 100.0 |

EXAMPLE 2

Two-Phase Sunscreen

A two-phase sunscreen (formulation 2) was made in accordance with the instant invention using the ingredients and weight percentages listed in Table 2 below. Formulation 2 also showed a two layer separation with an aqueous upper layer that is slightly hazy and an opaque, oily lower layer that is about 20% of the formula volume.

TABLE 2

Formulation 2 (All percentages in weight percent)

| Ingredients | % |
|---|---|
| Menthyl Anthranilate | 5.0 |
| Octyl Methoxycinnamate | 7.5 |
| Mineral Oil (70 ssu) | 2.5 |
| Dipropyleneglycol Dibenzoate | 5.0 |
| Deionized Water | 80.0 |
| Fragrance, Color, Preservative | QS |
| | 100.0 |

EXAMPLE 3

Three-Phase Sunscreens

Three-phase sunscreen compositions (formulations 3, 4, 5, and 6) were made in accordance with the instant invention using the ingredients and weight percentages listed in Table 3 below. Formulations 3 and 4 show the effect of changing the sunscreen agent. Formulation 3 is a three-layer system with a clear upper layer, a slightly hazy middle layer and a hazy bottom layer. The phase volume ratios, upper layer to middle layer to bottom layer, are 15% to 60% to 25%. Formulation 4 also shows three-layer separation with a clear upper layer and slightly hazy middle and bottom layers. The upper to middle to bottom layer phase volume separation ratio is 10% to 65% to 25%. Formulations 5 and 6 illustrate the effect of the addition of sodium chloride. Both formulations have extremely good layer separation and all layers are clear. The phase volume separation ratio of the upper layer to the middle layer to the bottom layer is about 20% to 40% to 40% for formulation 5 and 10% to 50% to 40% for formulation 6.

TABLE 3

(All percentages in weight percent) Formulations 3, 4, 5, and 6

| Ingredients | 3 % | 4 % | 5 % | 6 % |
|---|---|---|---|---|
| Menthyl Anthranilate | 5.0 | — | 5.0 | — |
| Octyl Methoxycinnamate | 7.5 | 7.5 | 7.5 | 7.5 |
| Benzophenone 3 | — | 5.0 | — | 5.0 |
| Cyclomethicone GE 1202 | 15.0 | 10.0 | 15.0 | 10.0 |
| Dipropyleneglycol Dibenzoate | 7.5 | 7.5 | 7.5 | 7.5 |
| Deionized Water | 55.0 | 60.0 | 52.0 | 57.0 |
| Ethanol | 10.0 | 10.0 | 10.0 | 10.0 |
| Sodium Chloride | — | — | 3.0 | 3.0 |
| Fragrance, Color, Preservative | QS | QS | QS | QS |
| | 100.0 | 100.0 | 100.0 | 100.0 |

EXAMPLE 4

Three-Phase Sunscreens

Three-phase sunscreen compositions (formulations 7, 8, 9, and 10) were made in accordance with the instant invention using the ingredients and weight percentages listed in Table 4 below. Formulations 7 through 10 show little effect from adding various humectants. All have clear upper layers that are about 10% of the formula volume, clear to slightly hazy middle layers that represent about 65% of the formula volume and clear to slightly hazy bottom layers that are about 25% of the formula volume. These formulations begin to show phase separation about one minute after shaking and complete (although not clear) phase separation in about ten to fifteen minutes. This separation time provides sufficient opportunity to apply the product before it is necessary to remix.

TABLE 4

(All percentages in weight percent)
Formulations 7, 8, 9 & 10

| Ingredients | 7 % | 8 % | 9 % | 10 % |
|---|---|---|---|---|
| Menthyl Anthranilate | 5.0 | 5.0 | 5.0 | 5.0 |
| Octyl Methoxycinnamate | 7.5 | 7.5 | 7.5 | 7.5 |
| Cyclomethicone GE 1202 | 12.5 | 12.5 | 12.5 | 12.5 |
| Dipropyleneglycol Dibenzoate | 5.0 | 5.0 | 5.0 | 5.0 |
| Deionized Water | 57.0 | 55.0 | 55.0 | 55.0 |
| Ethanol | 10.0 | 10.0 | 10.0 | 10.0 |
| Sodium Chloride | 3.0 | 3.0 | 3.0 | 3.0 |
| Glycerin | — | 2.0 | — | — |
| Propylene Glycol | — | — | 2.0 | — |
| Hexylene Glycol | — | — | — | 2.0 |
| Fragrance, Color, Preservative | QS | QS | QS | QS |
| | 100.0 | 100.0 | 100.0 | 100.0 |

EXAMPLE 5

Two and Three-Phase Sunscreens

Two phase (formulations 11 and 12) and a three-phase (formulation 13) sunscreen compositions were made in accordance with the instant invention using the ingredients and weight percentages listed in Table 5 below. Formulations 11 and 12 both have two clear phases. However, in formulation 11, the oily phase is at the top while in formulation 12 it is the bottom phase. Formulation 13 is a formulation where the water/alcohol phase is on top, the cyclomethicone phase is in the middle and the sunscreen/dipropyleneglycol dibenzoate phase is on the bottom and all are approximately equal in phase volume. (The phases are identified by using dyes that are only soluble in specific phases. For example: in this instance 0.04% of FD&C Blue No. 1 (1% aq soln.) and 0.4% of Crodarom Zi Cao were added. FD&C Blue No. 1 is an anionic water/alcohol soluble dye. Crodarom Zi Cao is a glyceryl tricaprate/caprylate extract of Lithospermum Officinale Root and is an oil soluble botanical extract and dyestuff. In addition, neither dye is soluble in cyclomethicone). Thus, a red, white (clear) and blue three-layered sunscreen was produced.

TABLE 5

(All percentages in weight percent)
Formulations 11, 12, and 13

| Ingredients | 11 % | 12 % | 13 % |
|---|---|---|---|
| Menthyl Anthranilate | 5.0 | 5.0 | 5.0 |
| Octyl Methoxycinnamate | 5.0 | 5.0 | 7.5 |
| Octyl Salicylate | 5.0 | 5.0 | — |
| Cyclomethicone GE1202 | 14.0 | 14.0 | 37.5 |
| Dipropyleneglycol Dibenzoate | 5.0 | 5.0 | 15.0 |
| Deionized Water | 50.0 | 40.0 | 17.5 |
| Ethanol | 10.0 | 20.0 | 17.5 |
| Sodium Chloride | 3.0 | 3.0 | — |
| Glycerin | 3.0 | 3.0 | — |
| Fragrance, Color, Preservative | QS | QS | QS* |
| | 100.0 | 100.0 | 100.0 |

It is to be understood by those skilled in the art that the foregoing descriptions and examples are illustrative of practicing the present invention, but are in no way limiting. Variations of the details presented herein may be made without departing from the spirit and scope of the present invention as defined by the following claims.

What is claimed is:

1. A multi-phase sunscreen composition comprising:
   (a) about 2% by weight to 15% by weight of a high-density aromatic ester having a specific gravity greater than about 1;
   (b) about 5% by weight to about 25% by weight of a sunscreen;
   (c) about 5% by weight to 25% by weight of one or more water-immiscible emollients; and
   (d) about 40% to 90% by weight of water or a mixture of water and a salt wherein (1) the composition comprises a first layer comprising the high-density ester and sunscreen; a second layer comprising water or water and a salt; and a third layer comprising one or more emollients, (2) the specific gravity of the first layer is greater than that of the second layer and the specific gravity of the second layer is greater than that of the third layer, (3) the first, second and third layers are substantially visually distinct, and (4) the first, second and third layers disperse upon mixing and separate between about one minute to fifteen munute after mixing.

2. The sunscreen composition of claim 1 wherein said composition excludes said salt and wherein the high-density ester is selected from the group consisting of benzoate and dibenzoate esters of diols, triols, and tetraols, $C_{12}$–$C_{15}$ alkyl benzoates, and castor-based benzoate esters.

3. The sunscreen composition of claim 2 wherein said composition excludes said salt and wherein the high-density ester is a benzoate ester of propylene glycol.

4. The sunscreen composition of claim 2 wherein said composition excludes said salt and wherein the high-density ester is a dibenzoate ester of dipropylene glycol.

5. The sunscreen composition of claim 1, wherein the composition is waterproof, water resistant, and sweat proof and has an SPF of between 2 and 50.

6. A multi-phase sunscreen composition comprising:
   (a) about 2% by weight to 15% by weight of a high-density aromatic ester having a specific gravity greater than about 1;
   (b) about 5% by weight to about 25% by weight of a sunscreen;
   (c) about 5% by weight to 25% by weight of one or more emollients and cyclic polyalkylsiloxanes; and
   (d) about 40% to 90% by weight of water wherein (1) the composition comprises a first layer comprising the high-density ester and sunscreen, a second layer comprised substantially of water, and a third layer comprising the emollient and cyclic polyalkylsiloxane, (2) the specific gravity of the first layer is greater than that of the second and third layers and the specific gravity of the second layer is greater than that of the third layer, (3) the first, second, and third layers are substantially visually distinct, and (4) the first, second, and third layer disperse upon mixing and separate between about one munute to fifteen minute after mixing.

7. The sunscreen composition of claim 6, wherein the high-density ester is selected from the group consisting of benzoate and dibenzoate esters of diols, triols, and tetraols, $C_{12}$–$C_{15}$ alkyl benzoates, and castor-based benzoate esters.

8. The sunscreen composition of claim 7, wherein the high-density ester is a benzoate ester of propylene glycol.

9. The sunscreen composition of claim 7, wherein the high-density ester is a dibenzoate ester of dipropylene glycol.

10. The sunscreen composition of claim 6, wherein each of the three layers has a substantially equal volume and is colored differently by addition of a dye that is soluble in that layer alone.

11. The sunscreen composition of claims 1, 2, 3, 6, or 7, wherein an emulsified layer forms at the interface of any two layers.

12. The sunscreen composition of claim 11, wherein the emulsified layer is stabilized by addition of one of more fumed silicas, hydrophobically treated fumed silicas, finely divided (powdered) polytetrafluoroethylene, microfine zinc oxide or microfine titanium dioxide.

13. The sunscreen composition of claim 1, 6 or 7 wherein the volume of the first layer comprises about 15% to 50% of the total sunscreen composition volume.

14. The sunscreen composition of claim 6 or 7, wherein the volume of the first layer comprises about 15% to 30% of the total sunscreen composition volume, the volume of the second layer comprises about 30% to 70% by volume of the total sunscreen composition, and the volume of the third layer comprises about 15% to 30% of the total sunscreen composition.

15. The sunscreen composition of claim 6 or 7 wherein the first, second, and third layers substantially separate into visually distinct layers between about ninety seconds to fifteen minutes after mixing.

16. The sunscreen compositions of claim 1, 6 or 7, wherein each of the layers is substantially clear prior to mixing.

17. A method of protecting the skin from UVA and UVB radiation comprising applying topically to the skin a sunscreen of claims 1, 2, 3, 6, or 7.

18. The method of claim 17, wherein the sunscreen has a SPF rating of 2 to 50.

19. The method of claim 18, wherein the sunscreen is waterproof, water resistant, and sweat proof and has an SPF rating of greater than 8.

* * * * *